United States Patent
Pérez-Willard

(10) Patent No.: US 9,857,318 B2
(45) Date of Patent: Jan. 2, 2018

(54) METHOD FOR GENERATING IMAGE DATA RELATING TO AN OBJECT AND PARTICLE BEAM DEVICE FOR CARRYING OUT THIS METHOD

(71) Applicant: Carl Zeiss Microscopy GmbH, Jena (DE)

(72) Inventor: Fabian Pérez-Willard, Aalen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/778,343

(22) PCT Filed: Mar. 18, 2014

(86) PCT No.: PCT/EP2014/055357
§ 371 (c)(1),
(2) Date: Sep. 18, 2015

(87) PCT Pub. No.: WO2014/147045
PCT Pub. Date: Sep. 25, 2014

(65) Prior Publication Data
US 2016/0274040 A1    Sep. 22, 2016

(30) Foreign Application Priority Data

Mar. 19, 2013    (DE) .................. 10 2013 204 829

(51) Int. Cl.
*G01N 23/04* (2006.01)
*G01N 23/225* (2006.01)
(Continued)

(52) U.S. Cl.
CPC ....... *G01N 23/046* (2013.01); *G01N 23/2255* (2013.01); *G01N 1/32* (2013.01);
(Continued)

(58) Field of Classification Search
USPC .......... 250/306, 307, 310, 311, 309
See application file for complete search history.

(56) References Cited

U.S. PATENT DOCUMENTS

| | | |
|---|---|---|
| 6,670,610 B2 | 12/2003 | Shemesh et al. |
| 7,312,448 B2 | 12/2007 | Principe |
| | (Continued) | |

FOREIGN PATENT DOCUMENTS

| | | |
|---|---|---|
| DE | 10 2007 026 847 A1 | 12/2008 |
| DE | 10 2008 040 426 A1 | 2/2010 |
| | (Continued) | |

OTHER PUBLICATIONS

English Translation of previously cited Reference CA—Glas-system, "3D Glasgravur intra3 von Glassystem: Wir sind darauf spezialisiert hochwertige Glasobjekte mittels dreidimensionaler Laserinnengravur zu veredeln; individuell nach den Wuenschen unserer Kunden," Ihr Unternehmen-praesentiert in seiner klarsten Form, Aug. 28, 2015, 1 pp.

(Continued)

*Primary Examiner* — Kiet T Nguyen
(74) *Attorney, Agent, or Firm* — Muirhead and Saturnell, LLC

(57) ABSTRACT

Generating image data of an object using a particle beam includes arranging at least one mark in the object or in a support material in which the object is embedded, determining a first examination region, exposing the first examination region by removing material of at least one of: the object and the support material, guiding a first particle beam over the first examination region, and acquiring image data of the first examination region using at least one detector by detecting interaction particles and/or interaction radiation due to an interaction of the first particle beam with the first examination region. Generating image data of an object using a particle beam may also include introducing the object into a support material in such a way that the object is partly or completely surrounded by the support material. A second examination region of the object may be determined relative to the mark.

22 Claims, 9 Drawing Sheets

(51) Int. Cl.
*G01N 1/32* (2006.01)
*G02B 21/00* (2006.01)

(52) U.S. Cl.
CPC .............. *G01N 2223/1006* (2013.01); *G01N 2223/418* (2013.01); *G01N 2223/419* (2013.01); *G01N 2223/6462* (2013.01); *G02B 21/008* (2013.01); *H01J 2237/31745* (2013.01)

(56) References Cited

U.S. PATENT DOCUMENTS

| | | | |
|---|---|---|---|
| 7,561,662 | B2 | 7/2009 | Wang et al. |
| 8,068,579 | B1 | 11/2011 | Yun et al. |
| 2007/0018099 | A1* | 1/2007 | Chitturi .............. G01B 15/08 250/310 |
| 2010/0059672 | A1 | 3/2010 | Zeile |
| 2010/0102223 | A1 | 4/2010 | Albiez et al. |
| 2010/0300873 | A1* | 12/2010 | Blackwood .............. G01N 1/32 204/192.33 |
| 2012/0305765 | A1 | 12/2012 | Zeile et al. |
| 2013/0279752 | A1 | 10/2013 | Thomas et al. |

FOREIGN PATENT DOCUMENTS

| | | |
|---|---|---|
| DE | 10 2008 041 815 A1 | 4/2010 |
| EP | 1 746 386 A2 | 1/2007 |
| EP | 1 443 541 B1 | 12/2008 |
| EP | 1 501 115 B1 | 7/2009 |
| EP | 2 383 768 A1 | 11/2011 |
| WO | WO 2010/136319 A1 | 12/2010 |
| WO | WO 2012/080363 A1 | 6/2012 |
| WO | WO 2013/006319 A1 | 1/2013 |

OTHER PUBLICATIONS

Glassystem, "3D Glasgravur intra3 von Glassystem: Wir sired darauf spezialisiert hochwertige Glasobjekte mittels dreidimensionaler Laserinnengravur zu veredeln; individuell nach den Wuenschen unserer Kunden," Ihr Unternehmen-praesentiert in seiner klarsten Form, Aug. 28, 2015, 1 pp.

Steve Wang, et al., "Metrology of 3D IC with X-ray Microscopy and Nano-scale X-ray CT," IEEE, 2009.
A. H. Voie, "Orthogonal-plane fluorescence optical sectioning: three-dimensional imaging of macroscopic biological specimens," Journal of Microscopy, Band 170, Pte 3, Jun. 1993, pp. 229-236.
Matthias Petzold, et al., "Micro Structure Analysis for System in Package Components—Novel Tools for Fault Isolation, Target Preparation, and High-resolution Material Diagnostics", paper presented in Las Vegas (NV), 2010 and published in Electronic Components and Technology Conference (ECTC), 2010 Proceedings 60th, pp. 1296-1302.
Jurgen A.W. Heymann, et al., "Site-specific 3D imaging of cells and tissues with a dual beam microscope", Journal of Structural Biology, Academic Press, United States, vol. 155, No. 1, Apr. 4, 2006, 63-73 (retrieved on Jul. 1, 2006).
P.R. Shearing, et al., "X-ray nano computerised tomography of SOFC electrodes using a focused ion beam sample-preparation technique", Journal of the European Ceramic Society, Elsevier Science Publishers, Barking, Essex, GB, vol. 30, No. 8, Mar. 4, 2010, 1809-1814.
Takahiro Sonomura, et al., "Correlative analysis of immunoreactivity in confocal laser-scanning microscopy and scanning electron microscopy with focused ion beam milling", Frontiers in Neural Circuits, vol. 7, Feb. 25, 2013, pp. 1-7.
Takeo Kamino, et al, "Application of a FIB-STEM system for 3D observation of a resin-embedded yeast cell," Journal of Electron Microscopy 53(5): 563-566, 2004.
Richard Wirth, "Focused Ion Beam (FIB) combined with SEM and TEM: Advanced analytical tools for studies of chemical composition, microstructure and crystal structure in geomaterials on a nanometer scale," Chemical Geology, 261, 2009, pp. 217-229.
Skyscan, "MICRO-CT IN SEM nondestructive volume visualization and measurement of objects internal microstructure in your SEM," 2007, pp. 8.
Cold Mounting brochure by Struers, Esbjerg/Denmark, 2008.
Glassystem, "3D Glasgravur intra3 von Glassystem: Wir sind darauf spezialisiert hochwertige Glasobjekte mittels dreidimensionaler Laserinnengravur zu veredeln; individuell nach den Wuenschen unserer Kunden," Ihr Unternehmen-praesentiert in seiner klarsten Form, Sep. 18, 2015, 1 pp.

* cited by examiner

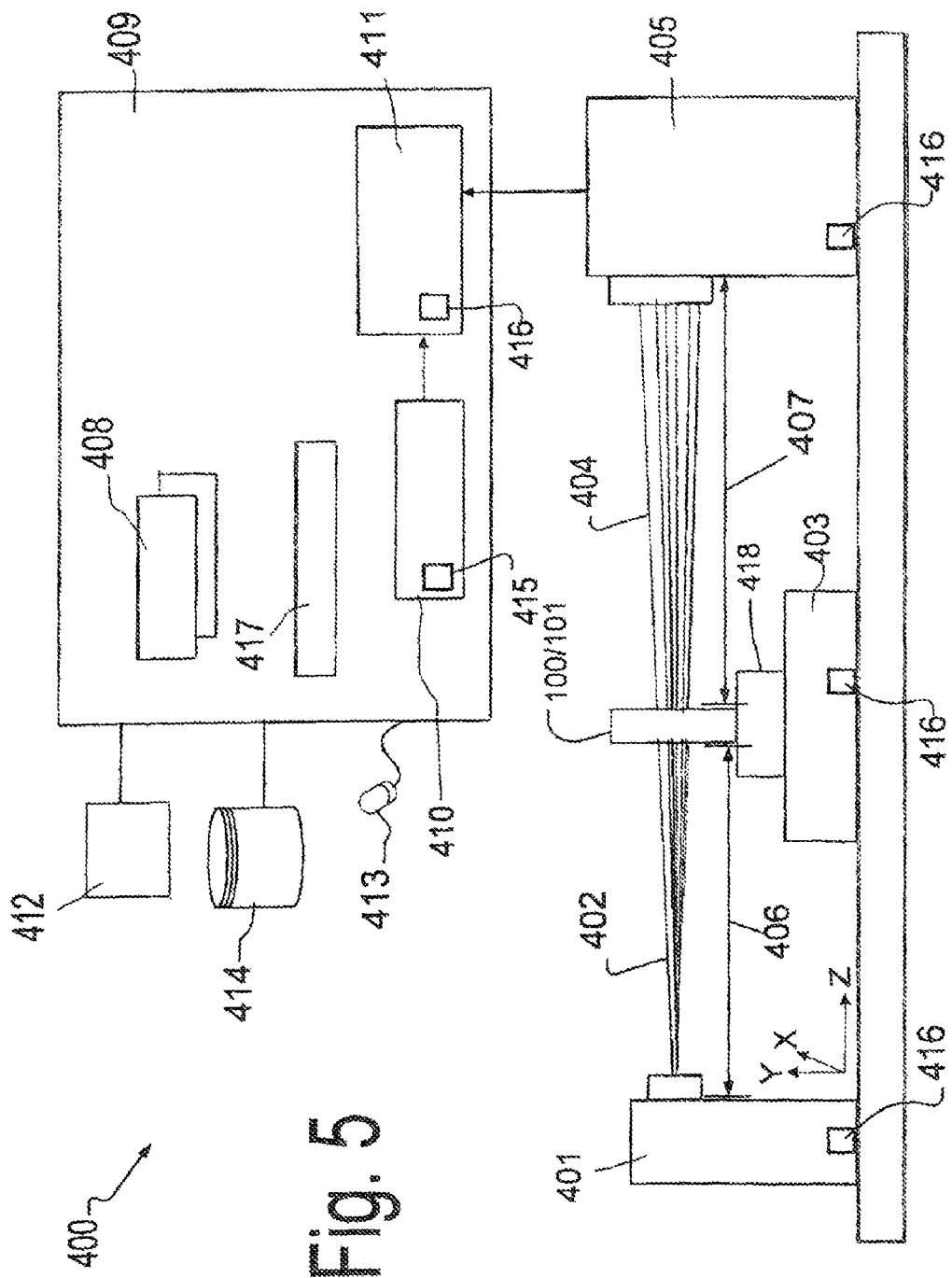

METHOD FOR GENERATING IMAGE DATA RELATING TO AN OBJECT AND PARTICLE BEAM DEVICE FOR CARRYING OUT THIS METHOD

TECHNICAL FIELD

The system described herein relates to a method for generating image data of an object and a particle beam device for carrying out this method. By way of example, the particle beam device is embodied as a combination device, which provides both an electron beam and an ion beam.

BACKGROUND OF THE INVENTION

Electron beam devices, in particular a scanning electron microscope (SEM) or a transmission electron microscope (TEM), are used to examine objects so as to obtain information in respect of the properties and behavior of these objects under certain circumstances.

In the case of an SEM, an electron beam (also referred to as primary electron beam below) is generated by means of a beam generator. The electrons in the primary electron beam are accelerated to a predeterminable energy and focused by a beam guidance system, in particular an objective lens, onto an object to be analyzed (a sample to be analyzed). A high-voltage source with a predeterminable acceleration voltage is used in the SEM for acceleration purposes. The primary electron beam is guided in a grid-shaped manner over a surface of the object to be analyzed by means of a deflection apparatus. Here, the electrons in the primary electron beam interact with the material of the object to be analyzed. In particular, interaction particles and/or interaction radiation is/are generated as a result of the interaction. By way of example, electrons are emitted from the object to be analyzed (so-called secondary electrons) and electrons from the primary electron beam are back-scattered at the object to be analyzed (so-called backscattered electrons). The secondary electrons and the backscattered electrons are detected and used for generating an image. An image of the object to be analyzed is obtained thus.

Imaging the object to be analyzed is one possible way of analyzing the object to be analyzed. However, further forms of analysis are known by all means. By way of example, the interaction radiation (in particular x-ray radiation or cathodoluminescence) is detected and analyzed in order to be able to draw conclusions about the composition of the object to be analyzed.

Furthermore, the prior art has disclosed the use of combination devices for processing and/or analyzing an object; in these, both electrons and ions can be guided onto an object to be processed and/or to be analyzed. By way of example, the practice of additionally equipping an SEM with an ion beam column is known. An ion beam generator arranged in the ion beam column is used to generate ions, which are used for processing an object (e.g. ablating a layer of the object or applying material onto the object) or else for imaging purposes. Here, the SEM serves, in particular, for observing the processing, but also for the further analysis of the processed or non-processed object.

Furthermore, the prior art has disclosed a particle beam device comprising a first particle beam column with a first beam axis, wherein the first particle beam column is embodied to generate a first particle beam. Additionally, the known particle beam device comprises a second particle beam column, which is provided with a second beam axis and embodied to generate a second particle beam. The first particle beam column and the second particle beam column are arranged in such a way in relation to one another that the first beam axis and the second beam axis include a first angle of approximately 50° to 60°. Furthermore, the known particle beam device has an object support which is rotatable about an axis of rotation. By way of example, the axis of rotation extends through the center of the object support. Furthermore, the axis of rotation includes a second angle with the first beam axis and a third angle with the second beam axis. An object on an object holder can be arranged on the object support, wherein the object has an object face to be processed and/or to be analyzed. The object holder is arranged above the object support along the axis of rotation.

In a known method, use is likewise made of both a first particle beam (ion beam) and a second particle beam (electron beam). The first particle beam is guided substantially perpendicularly to a marking surface of the object to be examined. Two longitudinal marks, arranged in a V-shaped manner in relation to a longitudinal axis of the object and intersecting at a point of the marking surface, are applied to the marking surface. Furthermore, by means of the first particle beam, provision is made for a layer of the object to be removed by scanning the first particle beam perpendicular to the longitudinal axis of the object. As a result of this, a surface which is oriented perpendicular to the longitudinal axis of the object (i.e. parallel to the first particle beam) is exposed. In a further step, the second particle beam impinges on the exposed surface. The interaction particles generated in the process are detected. The detection signals generated during the detection are used for imaging and the image data obtained thus are stored. The aforementioned method steps are repeated to expose further surfaces of the object to be examined and to obtain image data for the further surfaces. The stored image data of the various exposed surfaces are combined to form a three-dimensional image data record of the object in a subsequent process step.

In respect of the prior art, reference is made in an exemplary manner to DE 10 2008 041 815 A1, DE 10 2007 026 847 A1, EP 1 443 541 B1 and U.S. Pat. No. 7,312,448 B2.

The known particle beam devices from the prior art are used e.g. to carry out series examinations of an object. In particular, this is understood to mean that the object surface of an object is initially processed in a first step using the first particle beam. By way of example, material is ablated from the object face or material is deposited onto the object face. For the purposes of processing the object face, the object support is brought into a first position relative to the first particle beam column. The object face is subsequently processed using the first particle beam. In a second step, the processed object face is analyzed by means of the second particle beam. To this end, the object support is brought into a second position relative to the second particle beam column. The processed object face is subsequently analyzed. By way of example, the processed object face is imaged by means of the second particle beam. Provision is now made in the series examination for a multiple change between the first step and the second step. By way of example, the first position and the second position can be identical in this case. In this case, the second particle beam impinges e.g. obliquely onto the processed object face.

Moreover, the prior art has disclosed an x-ray microscope, in which an object is analyzed by means of x-ray beams. The interaction of the object with the x-ray beams is measured and evaluated. A representation of the object is obtained thus. A three-dimensional representation of the object can also be produced by means of the x-ray microscope. In respect of the prior art, reference is made in an exemplary manner to U.S. Pat. No. 7,561,662 B2 and the publication "Metrology of 3-D IC with X-ray Microscopy and Nanoscale X-ray CT" by Wang et al. in IEEE 2009.

Furthermore, the prior art has disclosed a confocal laser scanning microscope. Using the known confocal laser scanning microscope, a small region of an object to be analyzed is examined by means of a laser beam, wherein the laser beam is guided over the object in a grid-shaped manner. A representation of the object is calculated and displayed by evaluating the interaction of the laser beam with the object (in particular by means of measuring light reflected at, or transmitted through, the object or by means of fluorescence). In respect of the prior art, reference is made in an exemplary manner to the publication "Orthogonal-plane fluorescence optical sectioning: three-dimensional imaging of macroscopic biological specimens" by Voie et al. (Journal of Microscopy, volume 170, part 3, June 1993). Furthermore, WO 2010/136319 A1 has disclosed a combination of a particle beam device with a so-called SPI microscope (selective plane illumination microscope), which is used for correlative optical microscopy and particle beam microscopy. Moreover, WO 2012/080363 A1 has disclosed a method for automated imaging of predefined areas in section series, in which artificial structures in the form of bores are introduced into a still uncut object in order to simplify a subsequent reconstruction of the image of the object in 3-D.

For some objects to be examined, it is desirable for these objects to be analyzed to be examined with as many of the existing analysis methods and analysis devices as possible in order to collect as much information about the objects to be analyzed as possible.

It is therefore desirable to be able to examine an object in a simple manner with a plurality of analysis methods and analysis devices.

SUMMARY OF THE INVENTION

The method according to the system described herein serves to produce image data of an object to be analyzed by means of a particle beam. In the method according to the system described herein, provision is made of at least one mark being arranged in the object or in a support material, in which the object is embedded. Here arranging the mark is understood, both above and below, as e.g. applying the mark onto a surface of the support material and/or of the object. Additionally, or as an alternative thereto, the mark can also be arranged within the support material and/or the object. This will be discussed in more detail below. During an analysis of the object, the mark serves for orientation purposes such that regions of the object can easily and reliably be established and retrieved by different analysis methods or analysis devices. By way of example, the mark comprises a multiplicity of spaced apart individual marks, the distance between which is fixedly prescribed. In a further method step, there is a determination of at least one examination region of the object using the mark. By way of example, the examination region is a specific partial volume of the object, which is determined by a first analysis method and e.g. analyzed in more detail by a second analysis method. This will be discussed in even more detail below.

Once the examination region has been determined, the examination region is exposed by removing material of the object and/or of the support material. There can be different ways of exposing the examination region. Thus, provision is made in embodiments of the method according to the system described herein of the examination region being exposed by sawing, grinding, milling or by means of a laser. In a further embodiment, provision is made of using a particle beam for exposing the examination region. This will be discussed in more detail below. In addition to exposing the examination region, provision is made in once again other embodiments of the examination region being additionally prepared. By way of example, the examination region is polished and/or ground.

In the system described herein, provision is now made of a first particle beam being guided over the exposed examination region. In the process, there is an interaction between the particle beam and the exposed examination region. In particular, interaction particles (e.g. secondary particles or backscattered particles) and/or interaction radiation is/are produced. These are detected by means of at least one detector and converted into detector signals. The detector signals correspond to acquired image data of the exposed examination region.

In one embodiment of the method according to the system described herein, the object and/or the support material is/are embodied in a manner transparent to beams by means of which e.g. the examination region is determined. By way of example, the object and/or the support material is/are transparent to light beams in the visible range. Additionally, or as an alternative thereto, provision is made of the object and/or the support material being transparent to e.g. x-ray beams. Expressed differently, the object and/or the support material is/are embodied in such a way that x-ray beams can be transmitted through the object and/or the support material. Here it is possible, for example, for the object and/or the support material to be transparent to x-ray beams but not to be transparent to light beams in the visible range. In particular, it is sufficient for the support material to be transparent to the wavelength range of the radiation that is used in the subsequent selection or fixation of the examination region or transmissive to such a degree for the utilized radiation that a radiation detector arranged downstream of the object embedded in the support material can detect a sufficient radiation intensity.

In one embodiment of the method according to the system described herein, provision is alternatively or additionally made of the method comprising a step of introducing the object to the support material, with the object being introduced into the support material in such a way that the object is surrounded by the —e.g. transparent —support material. By way of example, the object is partly or completely surrounded by the support material. Expressed differently, the object is e.g. partly or completely encased by the support material. Partly or completely introducing the object to the analyzed into the support material (that is to say when the object to be analyzed is partly or completely encased by the support material) provides a simple option for examining the object to be analyzed by a plurality of analysis methods and/or analysis devices. Firstly, the object to be analyzed is simple to handle and it is easy to transport it between two different analysis devices, with the object moreover being protected due to the casing. Secondly, an examination region is easy to determine and always retrievable due to the arranged mark.

In a further embodiment of the method according to the system described herein, provision is made of the examination region of the object being determined with the aid of a tomographic method which supplies a three-dimensional data record of the object.

In a further embodiment of the method according to the system described herein, provision is made of the three-dimensional data record having a first spatial resolution R1, wherein the image data of the exposed examination region has a second spatial resolution R2, and wherein the following applies to the ratio of the first spatial resolution to the second spatial resolution R1/R2: 5<R1/R2<10 000.

In one embodiment of the method according to the system described herein, provision is made of the tomographic method comprising the following steps:
- irradiating the object a number of times in succession using x-ray radiation at different angles of incidence of the x-ray radiation on the object and detecting a sequence of images with the aid of the x-ray radiation respectively transmitted through the object,
- establishing the 3-D data record (i.e. the three-dimensional data record) of the object from the sequence of images by applying tomography evaluation software to the sequence of images,
- wherein the examination region is determined in the 3-D data record of the object,
- and wherein the marks are arranged in the object or in the support material in such a way that they are identifiable in the 3-D data record of the object.

In an in turn further embodiment of the method according to the system described herein, provision is made of the marks being arranged in such a way that at least some of the marks are still present even after the examination region has been exposed. In particular, provision is made of the marks being attached in such a way that some of the marks present after exposing the examination region are identifiable in the image data obtained by detecting interaction particles or interaction radiation, which is/are produced from the interaction of the first particle beam with the exposed examination region.

In one embodiment of the method according to the system described herein, provision is additionally or alternatively made of the introduction of the object into the—e.g. transparent—support material comprising the introduction of the object into a transparent plastic or into a glass. By way of example, PMMA, polycarbonate and/or a transparent epoxy resin is used as transparent plastic. By way of example, a commercially available industrial glass or crystal glass is used as glass. Alternatively, or in addition thereto, provision is made of the introduction of the object into the—e.g. transparent—support material comprising the introduction of the object into a glass or into a transparent plastic, which has a symmetric form. Introducing the object into a glass or into a transparent plastic with a symmetric form is advantageous in that the location of the object in the glass or in the transparent plastic is accurately determinable due to the symmetric form. By way of example, use can be made of symmetrically arranged edges and faces of the glass or of the transparent plastic for determining the location of the object in the glass or in the transparent plastic. In a further exemplary embodiment of the method according to the system described herein, provision is alternatively or additionally made of the object being introduced into a glass or into a transparent plastic, which has a cuboid or rectangular embodiment. By way of example, the glass or the transparent plastic has the form of a cuboid. However, reference is explicitly made to the fact that the invention is not restricted to the shape of a cuboid. Rather, the glass or the transparent plastic can have any suitable spatial form. By way of example, the glass or the transparent plastic has a cube-shaped or cylindrical embodiment.

In an embodiment of the method according to the system described herein, provision is additionally or alternatively made of arranging the mark on the object or on the—e.g. transparent—support material by means of a laser. Additionally, or as an alternative thereto, provision is made of arranging the mark on the object or on the—e.g. transparent—support material by means of a second particle beam, for example by means of an ion beam. Once again additionally, or as an alternative thereto, provision is made of arranging the mark on the object on a surface of the object or on the—e.g. transparent—support material on a surface of the support material. In a once again further advantageous embodiment of the method according to the system described herein, provision is additionally or alternatively made of arranging the mark by internal engraving of the object or of the—e.g. transparent—support material, for example by means of a laser. By way of example, this is brought about as explained below. In order to mark a corresponding point within the glass or the transparent plastic, a laser beam is focused into the interior of the glass or of the transparent plastic. At the focal point, the energy density of the laser beam is sufficiently high for visible points or structures to be produced at the focal point as a result of the interaction of the laser beam with the glass or the transparent plastic. Here, provision is made of the visible points or structures not being embodied as continuous openings for a first outer side of the glass or of the transparent plastic to a second outer side of the glass or of the transparent plastic.

In an in turn further embodiment of the method according to the system described herein, provision is additionally or alternatively made of determining the examination region of the object using an x-ray microscope. Additionally, or as an alternative thereto, provision is made of determining the examination region of the object using a confocal laser scanning microscope. These embodiments are advantageous in that, firstly, the examination region of the object is determined. Secondly, it is possible to obtain additional information about the object to be analyzed, which information is used for the analysis of the object, by means of these devices.

In one embodiment of the method according to the system described herein, provision is additionally or alternatively made of exposing the examination region using a laser beam of a laser processing apparatus and/or a second particle beam. By way of example, the second particle beam is an ion beam. This will be explained in yet more detail below.

In a further embodiment of the method according to the system described herein, provision is additionally or alternatively made of storing the acquired image data in a storage unit after exposing the examination region. Thus, the stored image data can be called, processed and/or analyzed at any time.

In an in turn further embodiment of the method according to the system described herein, provision is likewise additionally or alternatively made of the acquired image data of the exposed examination region being acquired as first image data. Furthermore, the following steps are carried out alternatively or additionally. Initially, the first image data are stored in a storage unit. Furthermore, a layer of the examination region (and possibly of the remaining object and of the—e.g. transparent—support material) is removed by means of a second particle beam and/or a laser beam. By way of example, the second particle beam is embodied as an ion beam. After removing the layer of the examination region, the first particle beam is moved over the now exposed surface of the examination region. Therefore, the first particle beam is focused onto the exposed face of the examination region after removing the layer. There is an acquisition of second image data by means of the detector by detecting interaction particles and/or interaction radiation due to an interaction between the first particle beam and the object. In particular, secondary particles and backscattered particles are produced. These are detected by the detector. The second image data are stored in the storage unit. By carrying out this embodiment repeatedly, it is possible to produce a three-dimensional representation of the examination region. To this end, there is a calculation of three-dimensional image data by means of the first image data and the second image data. Now, statements about the properties of the examination region can be made particularly well on the basis of the three-dimensional representation of the examination region.

In one embodiment of the method according to the system described herein, provision is additionally or alternatively made of an electron beam being used as the first particle beam. As already mentioned above, provision is made additionally or alternatively thereto of an ion beam being used as the second particle beam. By way of example, this embodiment of the method according to the system described herein is carried out in a combination device, which has both an electron beam column and an ion beam column.

In a further embodiment of the method according to the system described herein, provision is made of a crack in a material or a defect of a semiconductor being determined as examination region. This will be explained in more detail below.

In an even further embodiment of the method according to the system described herein, provision is made of a TEM lamella, which has the examination region, being generated using the second particle beam. The TEM lamella is then irradiated by means of the first particle beam. Particles of the first particle beam transmitted through the TEM lamella are detected by a further detector.

In an in turn further embodiment of the method according to the system described herein, provision is made of the object initially being examined by means of a confocal laser scanning microscope, of the object being stained and/or fixed after the examination and of the examination region being determined after staining and/or fixation by using an x-ray microscope. Subsequently, the examination region is exposed and the image data of the exposed examination region are acquired.

The system described herein also relates to computer program product with an executable program code, which is loadable (or loaded) into a processor and, when executed, executes a method which has at least one of the aforementioned steps, or steps yet to be mentioned below, or a combination of at least two of the steps either mentioned above or yet to be mentioned below.

Moreover, the system described herein relates to a particle beam device for carrying out a method, which has at least one of the aforementioned steps or steps yet to be mentioned below. The particle beam device comprises at least one first beam generator for generating a first particle beam, at least one first objective lens for focusing the first particle beam onto the object and at least one control unit with a processor, in which a computer program product, as already described above, is loaded.

In a further embodiment of the particle beam device according to the system described herein, provision is additionally or alternatively made of the particle beam device comprising at least one second beam generator for generating a second particle beam and at least one second objective lens for focusing the second particle beam onto the object. By way of example, the first particle beam is embodied as an electron beam. Furthermore, the second particle beam is e.g. embodied as an ion beam. Alternatively, or in addition thereto, provision is made of the particle beam device having a laser apparatus for generating a laser beam.

BRIEF DESCRIPTION OF THE DRAWINGS

Below, the system described herein will be explained in more detail on the basis of exemplary embodiments by means of the figures. Here:

FIG. 5 shows a schematic illustration of an embodiment of an x-ray tomography system.

DETAILED DESCRIPTION OF VARIOUS EMBODIMENTS

Figure 1A:
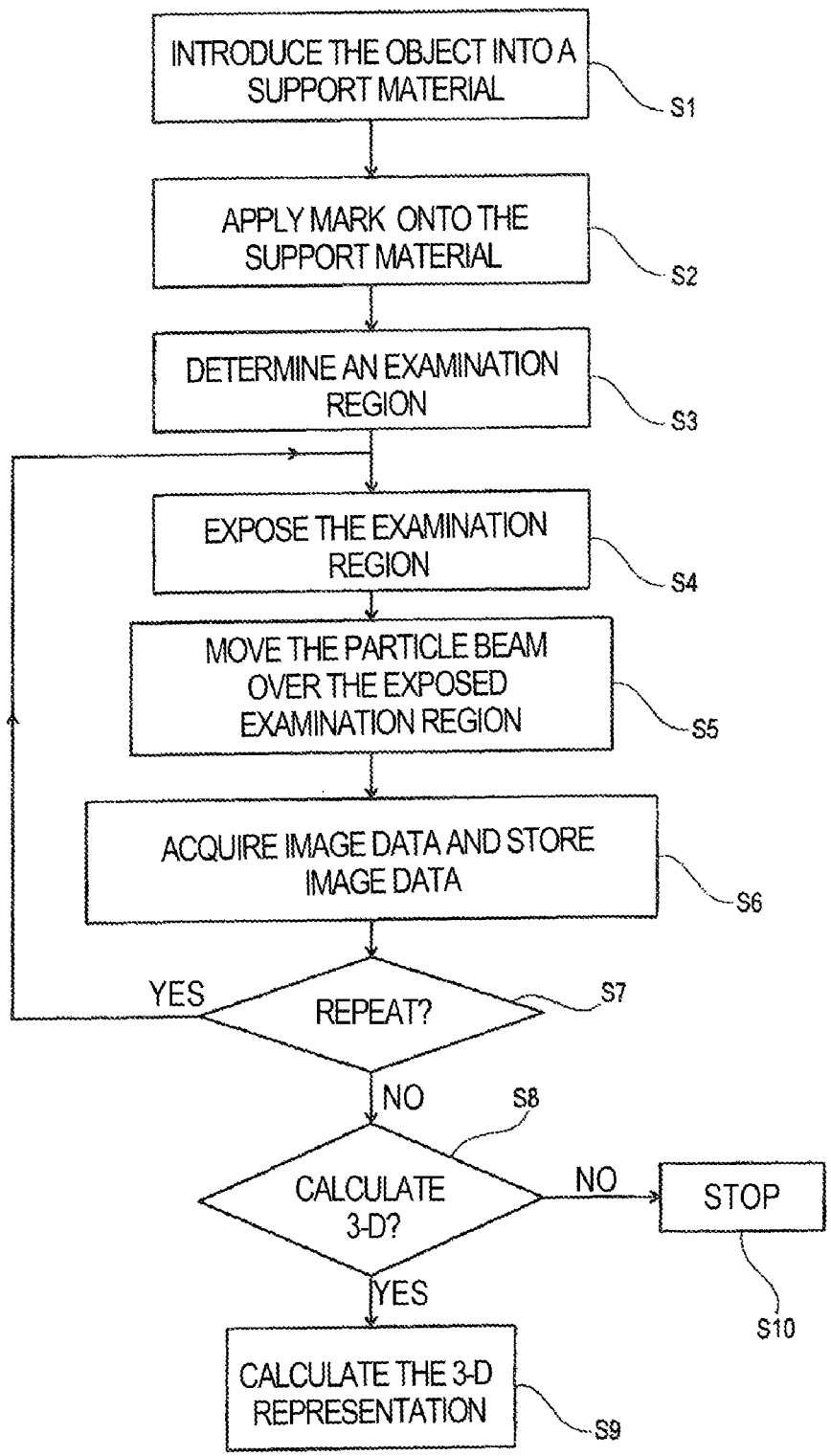
FIGS. 1A to 1D show schematic illustrations of flows of embodiments of the method.
Figure 2:
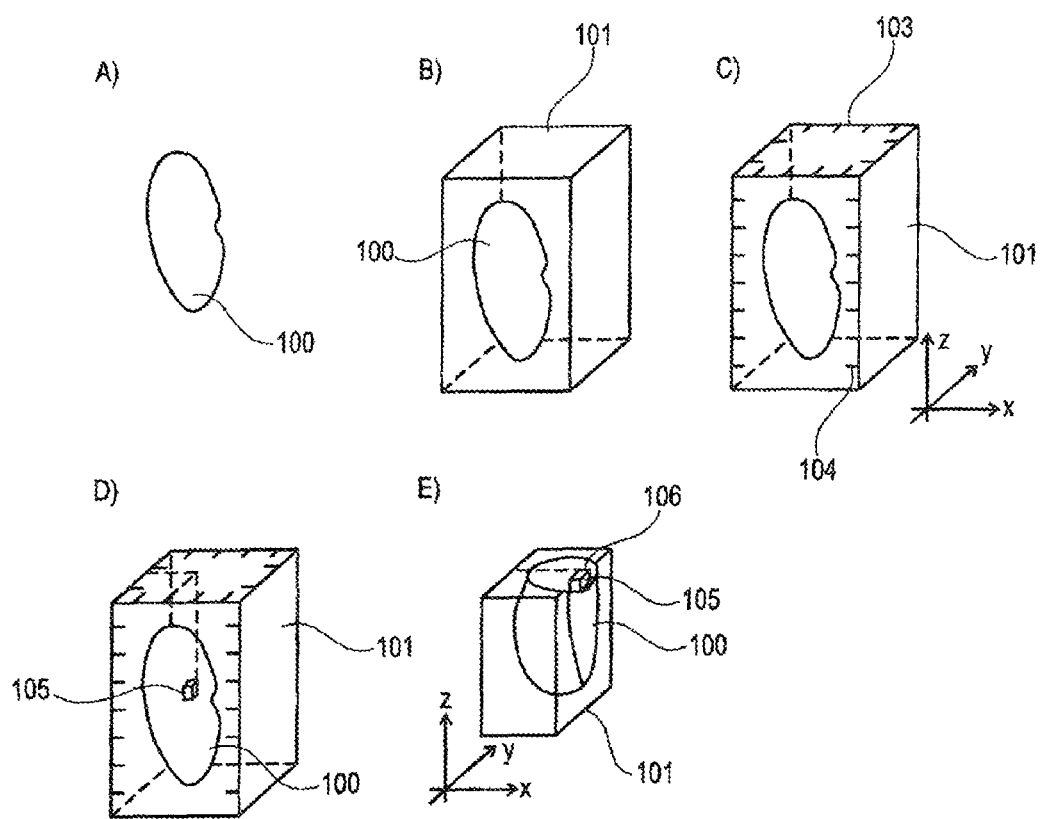
FIG. 2 shows illustrations of a transparent support material and of the object during different method steps.

FIG. 1A shows a schematic illustration of a first embodiment of the method according to the system described herein. FIG. 2 shows illustrations for elucidating individual method steps.

In method step S1, an object 100 is introduced into a transparent support material 101 (cf. FIGS. 2A and 2B). Here, the object 100 is introduced into the transparent support material 101 in such a way that the object 100 is partly or completely surrounded by the transparent support material 101. In the embodiment depicted in FIG. 2B, the object 100 is completely surrounded by the transparent support material 101. In other words, the object 100 is completely encased by the transparent support material 101. In the exemplary embodiment depicted here, a transparent plastic (e.g. PMMA, polycarbonate, epoxy resin or polyester resin) or a glass (e.g. an industrial glass or a crystal glass) is used as transparent support material 101. In the exemplary embodiment depicted here, the transparent support material 101 has a symmetric form in the form of a cuboid. This is advantageous in that the relative location of the object 100 in the transparent support material 101 can easily be determined. By way of example, the edges and faces of the transparent support material 101 can be used for determining the location of the object 100 in the transparent support material 101. However, the invention is not restricted to the form of a cuboid described above. Rather, any suitable form of the transparent support material 101 can be selected for the invention, for example the form of a cylinder, a cone, a frustum, a pyramid or further spatial structures.

In a further method step S2, a mark 103 is applied to the transparent support material 101 (cf. FIG. 2C). The mark 103 serves for orientation purposes when analyzing the object 100 such that regions of interest of the object 100 can easily and reliably be established and retrieved by different analysis methods or analysis devices. By way of example, the mark 103 comprises a multiplicity of individual marks 104 at a distance from one another, the distance between said marks being fixedly predetermined (cf. FIG. 2C). The individual marks 104 extend along the edges of the transparent support material 101. The individual marks 104 are applied e.g. by means of internal engraving. A laser beam is focused into the interior of the glass or of the transparent plastic in order to mark a corresponding point within the glass or transparent plastic. At the focal point, the energy density of the laser beam is sufficiently high so that visible points or structures in the focal point are produced due to the interaction of the laser beam with the glass or the transparent plastic. The advantage of internal engraving is that the individual marks 104 generally are not also ablated when material of the object 100 is ablated. Furthermore, the individual marks 104 can be arranged relatively close to the object 100 such that a good identification of regions of the object 100 by means of the individual marks 104 is possible.

In addition or as an alternative to the internal engraving described above, provision is made in the exemplary embodiment in accordance with FIG. 2C of the mark 103 being applied to the surface of the transparent support material 101.

In one embodiment of the method according to the system described herein, provision is made of the application of the mark 103 on the transparent support material 101 being brought about by means of a laser. Additionally, or as an alternative thereto, provision is made of the application of the mark 103 on the transparent support material 101 being brought about by means of an ion beam. By way of example, this can be brought about in a particle beam device 200, which is explained in more detail below on the basis of FIG. 3A.

Figure 3A:
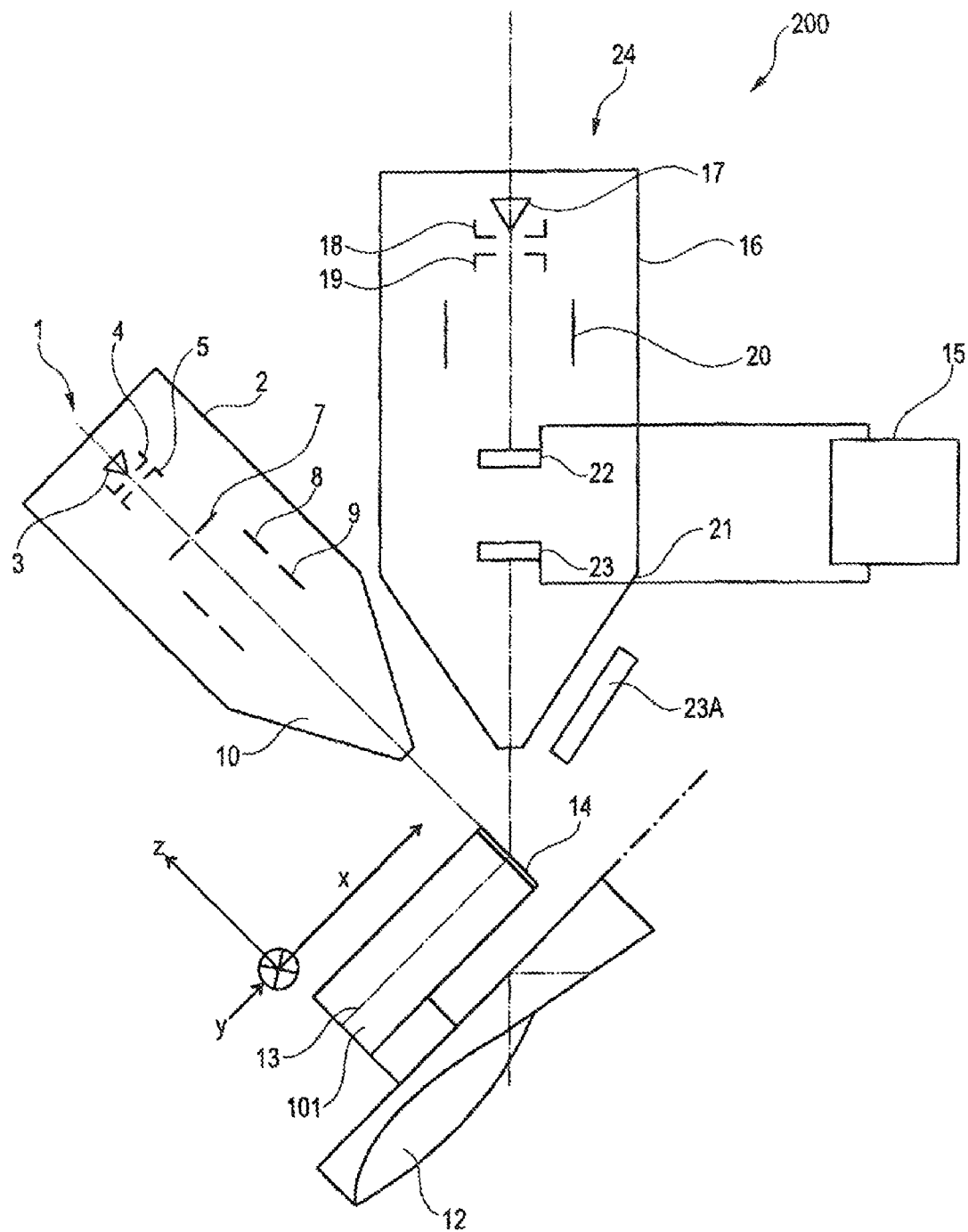
FIG. 3A shows a first embodiment of a particle beam device for carrying out numerous method steps.

FIG. 3A shows a schematic illustration of the particle beam device 200 which has an ion beam device 1 and an electron beam device 24.

The ion beam device 1 has an ion beam column 2, in which numerous units of the ion beam device 1 are arranged. In particular, an ion source 3 is arranged in the ion beam column 2. Ions, which form a particle beam in the form of an ion beam in the ion beam column 2, are generated by means of the ion source 3. By way of example, ions from a single element (e.g. gallium (Ga)) are provided by the ion source 3. The ions can be embodied as ionized atoms, or else as ionized molecules.

The ions are accelerated to a pre-determinable potential by means of an ion beam electrode 4 and subsequently guided through a first condenser lens 5. Subsequently, the ion beam formed from the ions is guided through a stop 7 and then reaches a first electrode apparatus 8 and a second electrode apparatus 9, which are embodied as scanning electrodes. The ion beam consisting of ions is scanned over the transparent support material 101 by means of the first electrode apparatus 8 and the second electrode apparatus 9. Before this, the ion beam is focused onto the transparent support material 101 by means of a first objective lens 10. Reference is made to the fact that the transparent support material 101 is not transparent to the ion beam, but only to light beams incident on the transparent support material 101 which have a wavelength in the visible range, or to the x-ray radiation incident on the transparent support material 101.

Beforehand, the transparent support material 101 is arranged on a sample holder 12, which ensures that the transparent support material 101 is movable along an x-axis. In this exemplary embodiment, the x-axis extends along a longitudinal axis 13 of the transparent support material 101, as is depicted in FIG. 3A. The x-axis can also have a different arrangement in further exemplary embodiments. The longitudinal axis 13 of the transparent support material 101 preferably lies in a first plane which is arranged perpendicular, or substantially perpendicular, to a second plane in which the ion beam is fed to the transparent support material 101.

The electron beam device 24 is embodied as a scanning electron microscope. It has an electron column 16, in which the units of the electron beam device 24 are arranged. Thus, provision is made of an electron source 17, which generates electrons that are extracted by means of a first electrode 18. The electrons are accelerated to a pre-determinable potential by means of a second electrode 19. The electrons are subsequently guided through a second condenser lens 20, as a result of which a second particle beam in the form of an electron beam is formed. Said beam is focused on a surface 14 of the transparent support material 101 by means of a second objective lens 21. Scanning electrodes (not depicted) arranged at the second objective lens 21 ensure that the electron beam can be scanned over the transparent support material 101.

When the electron beam impinges on the surface 14 of the transparent support material 101, interaction particles, in particular secondary electrons and backscattered electrons, are produced. These are detected by means of a first detector 22 and by means of a second detector 23 and used for imaging. It is therefore possible to generate an image of the surface 14 of the transparent support material 101. The first detector 22 and the second detector 23 are connected to an evaluation and storage unit 15, in which image data of the surface 14 is analyzed and stored. Furthermore, the evaluation and storage unit 15 is provided with a processor, into which a program code of a computer program product is loaded, which executes the methods in accordance with the system described herein. In further exemplary embodiments, provision can furthermore be made for a third detector 23A (cf. FIG. 3A), which registers further interaction reactions, e.g. x-ray quanta, which can likewise be used for generating image data.

The mark 103 is now applied onto the transparent support material 101 by means of the particle beam device 200 depicted in FIG. 3A. To this end, the ion beam is guided to the faces of the transparent support material 101, at which the mark 103 is intended to be arranged, and the mark 103 is arranged at the transparent support material 101 by means of material processing (e.g. a material ablation or material deposition). Arranging the mark 103 on the transparent support material 101 can be observed by means of imaging by the electron beam.

Figure 3B:
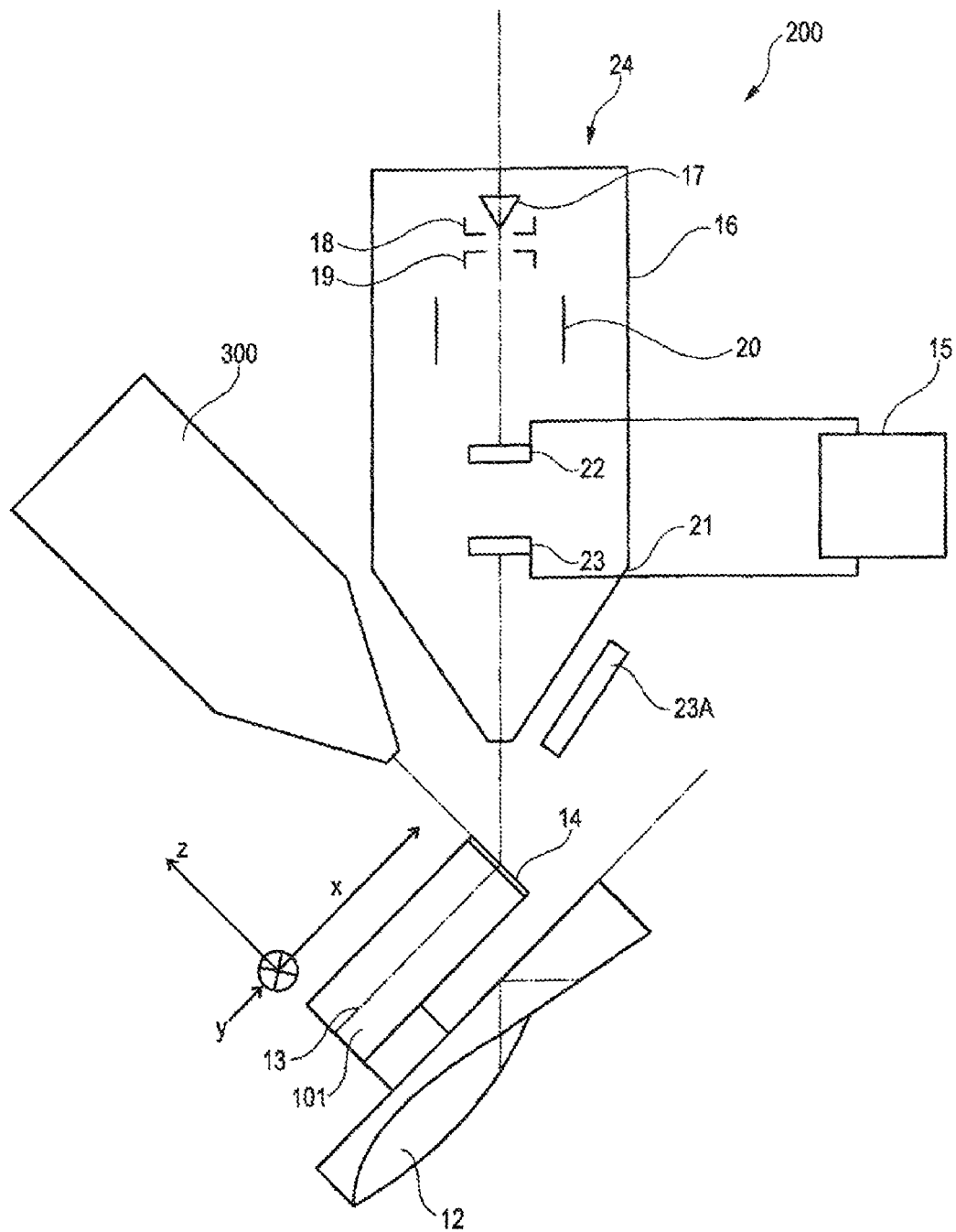
FIG. 3B shows a second embodiment of a particle beam device for carrying out numerous method steps.

A further embodiment of the particle beam device 200 according to the system described herein is depicted in FIG. 3B. FIG. 3B is based on FIG. 3A. The same components are denoted by the same reference signs. In contrast to the exemplary embodiment in FIG. 3A, the exemplary embodiment in FIG. 3B does not have an ion beam device 1, but rather a laser unit 300 with a laser. In this exemplary embodiment, the laser unit 300 is used to apply the mark 103 onto the transparent support material 101 or introduce said mark by internal engraving into the transparent support material 1. To this end, reference is made to the explanations above.

In a further method step S3, a region of the object 100, which is intended to be examined in more detail, is now determined (FIG. 1A). This region is referred to as an examination region 105. By way of example, the examination region 105 is a certain partial volume of the object 101 (cf. FIG. 2D). The examination region 105 can be determined in different ways. In one embodiment of the method, provision is made of the transparent support material 101 being introduced into an x-ray microscope and the object 100 being examined by means of the x-ray microscope. The examination region 105 is then also determined during this examination. In a further embodiment of the method, provision is made of the transparent support material 101 being introduced into a confocal laser scanning microscope and the object 100 being examined by means of the confocal laser scanning microscope. The examination region 105 is then determined during this examination. The two embodiments are advantageous in that, firstly, the examination region 105 of the object 101 is determined. Secondly, the two microscopes can be used to obtain additional information about the object 100, which is used for analyzing the object 100. By way of example, provision can be made in all exemplary embodiments for determining the examination region 105 of data established in the determination, in particular image data, being stored in a storage unit. By way of example, the stored data are used for correlation with further data which are only registered subsequently.

A three-dimensional data record (3-D data record) with a resolution that is reduced in relation to the resolution of the particle beam device 200 can be recorded in method step S3. This can be brought about by means of a laser scanning microscope in such a way that the object 100, which is embedded in the support material 101, is scanned by the focused laser beam of the laser scanning microscope in all three mutually perpendicular spatial directions and image information is recorded and stored by detecting reflected light or fluorescence light at each scanning point in the three-dimensional space, and said image information is subsequently assembled to form a 3-D data record of the object 100. Alternatively, the 3-D data record in method step S3 can also be recorded by way of an x-ray microscope or an x-ray tomography system, e.g. an x-ray micro-tomography system or an x-ray nano-tomography system, by virtue of the object 100, which is embedded in the support material 101, being irradiated by x-ray radiation and the transmitted x-ray radiation being detected. Then, like in computed tomography, a plurality of images of the transmitted x-ray radiation are recorded from different transmission directions through the object 100, which is embedded in the support material 101, for example by virtue of the object 100, which is embedded in the support material 101, being rotated relative to the x-ray source and the x-ray detector between the individual image recordings. A 3-D data record of the object 100, which is embedded in the support material 101, can then be obtained by a tomographic evaluation of the recorded images.

Then, in method step S3, the region or the regions, which is/are intended to be examined in more detail, are determined with the resolution and the accuracy of the method used in method step S3 for the generation of the 3-D data record. If the 3-D data record is obtained by a laser scanning microscope, the resolution or the setting of the region to be examined in more detail is typically 200 nm-500 nm. If the 3-D data record is obtained by an x-ray microscope with x-ray imaging between the object 100 and the detector, the resolution or the setting of the region to be examined in more detail is typically 10 nm-5000 nm. If the 3-D data record is obtained with an x-ray microscope without x-ray imaging between the object 100 and the detector, i.e. by means of an x-ray micro-tomography system or an x-ray nano-tomography system, the resolution or setting of the region to be examined in more detail is typically 500 nm to 5000 nm. In all the aforementioned cases, the region to be examined in more detail or the regions to be examined in more detail are set with an accuracy that is less than the resolution of 0.1 nm to 5 nm, with which the object 101 is subsequently examined by means of the particle beam device 200 by a factor of 5 to 5000 or a factor of 5 to 10,000 or by a factor of 2 to 50,000.

In a further method step S4 (cf. FIG. 1A), the examination region 105 is now exposed (cf. FIG. 2E). The examination region 105 can be exposed in different ways. Thus, in embodiments of the method according to the system described herein, provision is made of the examination region 105 to be exposed by sawing, grinding, milling or by means of a laser unit. In a further embodiment, provision is additionally made of the transparent support material 101 being introduced together with the object 100 into the particle beam device 200 in accordance with FIG. 3A and of using the ion beam for exposing the examination region 105. By means of the ion beam, it is possible to ablate the material of the transparent support material 101 and the material of the object 100 layer-by-layer, until a surface 106 of the examination region 105 is exposed and it is possible to subject the latter to further analysis. Additionally, or as an alternative thereto, provision is made of the transparent support material 101 being introduced together with the object 100 into the particle beam device 200 in accordance with FIG. 3B and of using the laser beam for exposing the examination region 105.

In all these cases, the region to be examined in more detail or the regions to be examined in more detail is/are exposed on the basis of the 3-D data record or 3-D data records obtained in method step S3 and the mark 103 applied onto the transparent support material 101 or introduced into the transparent support material 101. To this end, it is necessary for the mark 103 applied onto the support material 101 or introduced into the support material 101 to be identifiable in the respectively recorded images and in the 3-D data record obtained in method step S3, both in the method used in method step S3 and in the observation method used during the exposure process. Thus, the exposure of the region to be examined in more detail or the regions to be examined in more detail is then brought about with an accuracy which corresponds to the resolution of the method used in method step S3.

For the further analysis, provision is made in the embodiment of the method according to the system described herein, as explained here, of the examination region 105 being analyzed in the particle beam device 200 in accordance with FIG. 3A or 3B. To this end, the electron beam is scanned over the exposed surface 106 of the examination region 105 in method step S5. When the electron beam impinges on the surface 106 of the examination region 105, interaction particles, in particular secondary electrons and backscattered electrons, are produced. These are detected by means of the first detector 22 and by means of the second detector 23 and used for imaging. Thus, it is possible to generate an image of the surface 106 of the examination region 105. The first detector 22 and the second detector 23 are connected to the evaluation and storage unit 15, in which image data of the surface 106 of the examination region 105 are registered, analyzed and stored in a method step S6.

Alternatively, or in addition thereto, it is also possible to use the ion beam for analyzing the examination region 105 in the particle beam device 200 in accordance with FIG. 3A. To this end, the sample holder 12, on which the transparent support material 101 is arranged together with the object 100, is oriented in such a way that the surface 106 of the examination region 105, and therefore the surface 14 in accordance with FIG. 3A, is approximately perpendicular or the transparent support material 101 is aligned obliquely in relation to the ion beam of the ion beam column 2. Interaction particles, e.g. secondary electrons or secondary ions, are produced by the impact of the ion beam. By way of example, the secondary electrons are detected by the detectors 22 and 23, which were already described above, and are then used for imaging and storing image data. The secondary ions are detected by means of e.g. the third detector 23A or a further ion detector (not depicted here) and are subsequently analyzed.

If the transparent support material 101 and/or the object 100 are made of a nonconductive or badly conductive material, provision is made in a further embodiment of the system described herein of measures being taken after, or during, method steps S5 and S6 for removing or minimizing charging effects. By way of example, these methods are known from DE 10 2008 040 426 A1 and EP 1 501 115 B1.

A check is now carried out in a further method step S7 as to whether further image data of the examination region 105 is intended to be generated (cf. FIG. 1A). If this is the case, method steps S4 to S7 are repeated. In this repetition, a layer of the examination region 105 (and optionally of the remaining object 100 and of the transparent support material 101) is removed in method step S4 by means of the ion beam in the particle beam device 200 of FIG. 3A or by means of the laser beam in the particle beam device 200 of FIG. 3B. After the layer is removed, a further surface 106 of the examination region 105 is exposed in turn, onto which further surface the electron beam is focused and over which further surface the electron beam is moved. There is acquisition of image data of the further surface 106 and storing of these image data, as already explained above.

If image data are no longer intended to be acquired, a check is carried out in method step S8 as to whether a three-dimensional representation of the examination region 105 is intended to be calculated (cf. FIG. 1A). If this is desired, a three-dimensional representation of the examination region 105 is calculated in method step S9 using the stored image data and it is displayed in a display unit (cf. FIG. 1A). If no calculation of a three-dimensional representation is desired, the method is stopped in method step S10 (cf. FIG. 1A).

When the marks 103 are applied or introduced in method step S2, the marks 103 should be distributed so evenly over the object 100 or the support material 101 that it is highly probable that a sufficient number of marks 103 are present in the examination region 105 to be determined later. It is therefore expedient to carry out a check after setting the examination region 105 and prior to exposing the examination region 105 as to whether the examination region 105 has a sufficient number of marks 103. If this is not the case, it may be expedient prior to exposing the examination region 105 to once again apply or introduce additional marks 103 in the examination region 105 or in the support material 101 directly surrounding the examination region 105 such that these marks 103 are still present and identifiable, even after the examination region 105 has been exposed.

Figure 1B:
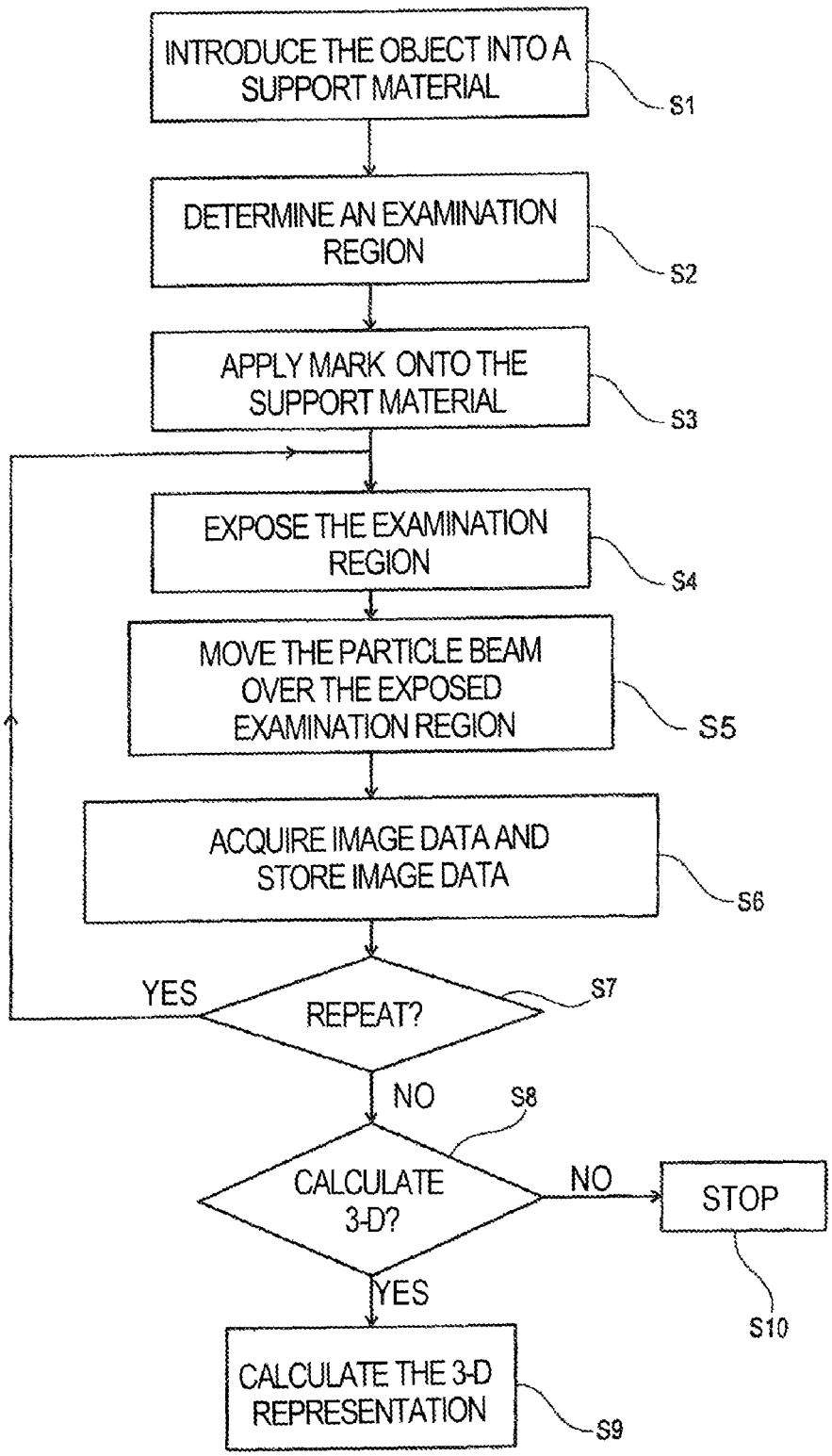

A sequence of a further exemplary embodiment of the method according to the system described herein is depicted in FIG. 1B. The exemplary embodiment of FIG. 1B is based on FIG. 1A. However, the exemplary embodiment of FIG. 1B is different in that the examination region 105 is determined in method step S2 and the mark 103 is applied/arranged in the transparent support material 101 in method step S3. Here too, it is possible when determining the examination region 105 for e.g. the data, in particular image data, established during the determination, to be stored in a storage unit. By way of example, the stored data are used for the correlation with further data, which are only acquired later. An advantage of this exemplary embodiment is that it can be easier to ensure that, after the examination region 105 is exposed, a sufficient number of marks 103 are available in the examination region 105 or the direct vicinity thereof.

Figure 1C:
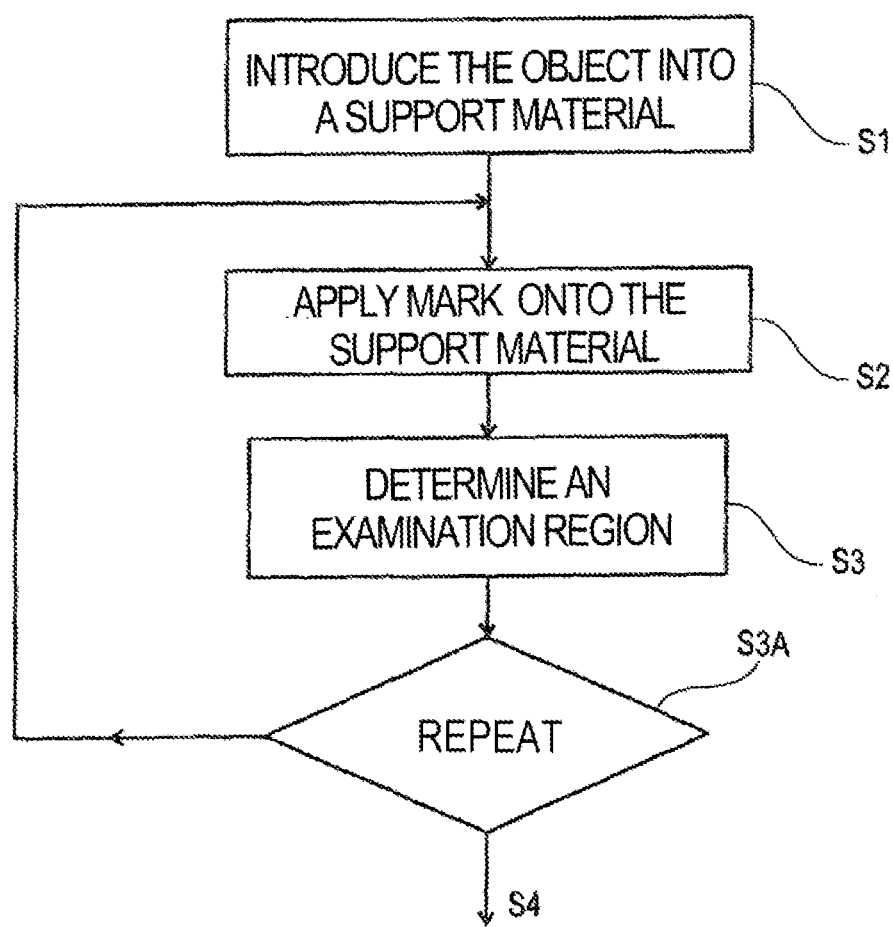

A sequence of an in turn further exemplary embodiment of the method according to the system described herein is depicted in FIG. 1C. The exemplary embodiment of FIG. 1C is based on FIG. 1A. However, the exemplary embodiment of FIG. 1C is different in that method step S3 is followed by method step S3A, in which there is a query as to whether the application of the mark 103 (method step S2) and the determination of the examination region 105 (method step S3) is intended to be carried out again. By way of example, this exemplary embodiment is selected for applying more accurate and finer individual marks 104. If a repetition is not wanted, this is followed by method step S4 from FIG. 1A and the further method steps following method step S4.

Figure 1D:
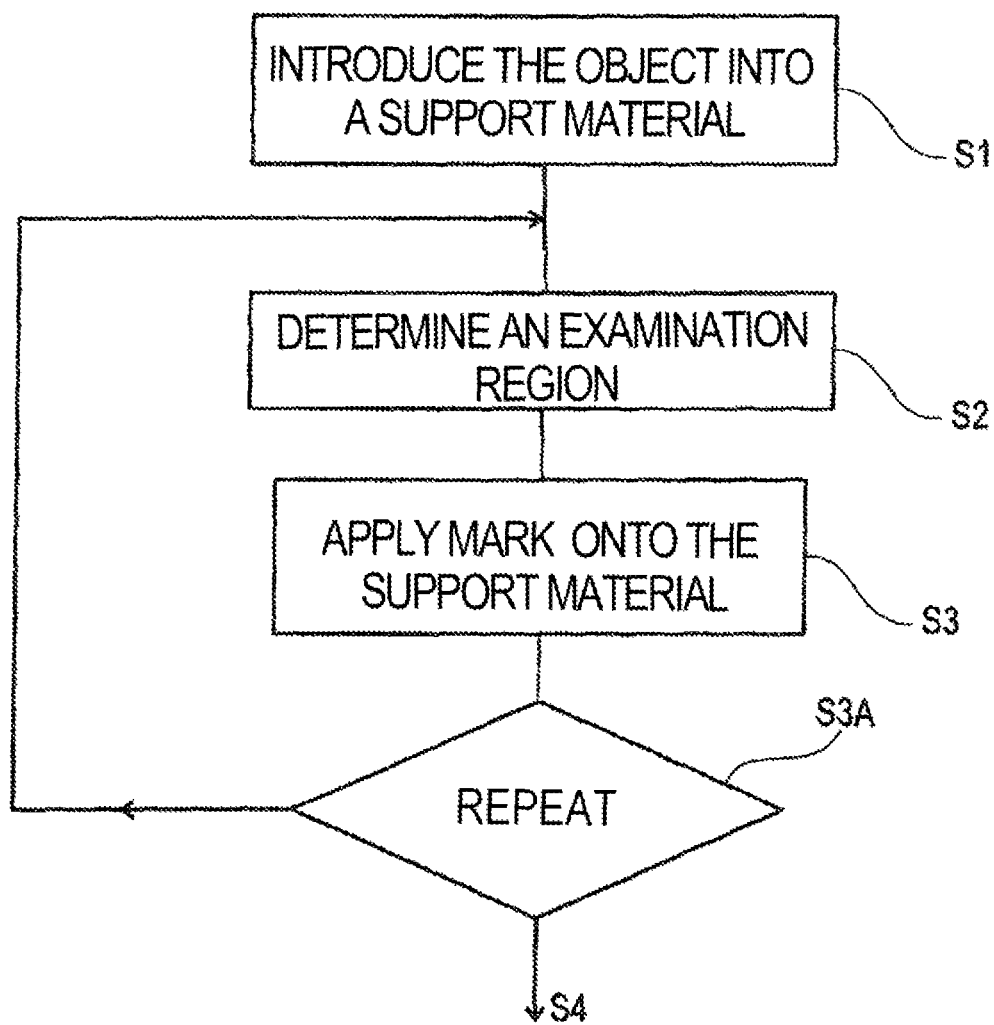

A sequence of an in turn further exemplary embodiment of the method according to the system described herein is depicted in FIG. 1D. The exemplary embodiment of FIG. 1D is based on FIG. 1B. However, the exemplary embodiment of FIG. 1D is different in that method step S3 is followed by method step S3A, in which there is a query as to whether the determination of the examination region 105 (method step S2) and the application of the mark 103 (method step S3) are intended to be carried out again. By way of example, this exemplary embodiment is selected for applying more accurate and finer individual marks 104. If a repetition is not wanted, this is followed by method step S4 from FIG. 1B and the further method steps following method step S4.

The explained exemplary embodiments of the method according to the system described herein have all advantages and properties that were already explained further above. Reference is explicitly made thereto at this juncture.

What is common to all methods described above is that, after introducing the object 100 into the transparent support material 101 and the subsequent application or introduction of the mark 103 onto or into the transparent support material 101, a 3-D tomography method is initially used to obtain a 3-D data record with a resolution that is reduced in relation to the resolution of the particle beam device 200, but nevertheless high in the range between 10 nm and 5000 nm, of the object 100, which is embedded into the transparent support material 101, such that the subsequent exposure of the object region to be examined in more detail or the object regions to be examined in more detail can take place quickly using a relatively coarse method or with relatively coarse steps using the mark 103 applied onto the transparent support material 101 or introduced into the transparent support material 101. Subsequently, this is followed by obtaining in each case a 3-D data record with a high resolution in the range of 0.1 nm to 5 nm of the region to be examined in more detail or of the regions to be examined in more detail with the aid of the particle beam device 200, wherein the production of the 3-D data record removes successive layers of the region 105 to be examined in more detail and respectively records an image using the particle beam device 200. Here, the 3-D tomography method allows the 3-D data record for the object 100 and the transparent support material 101 to be obtained in a nondestructive manner.

Figure 4:
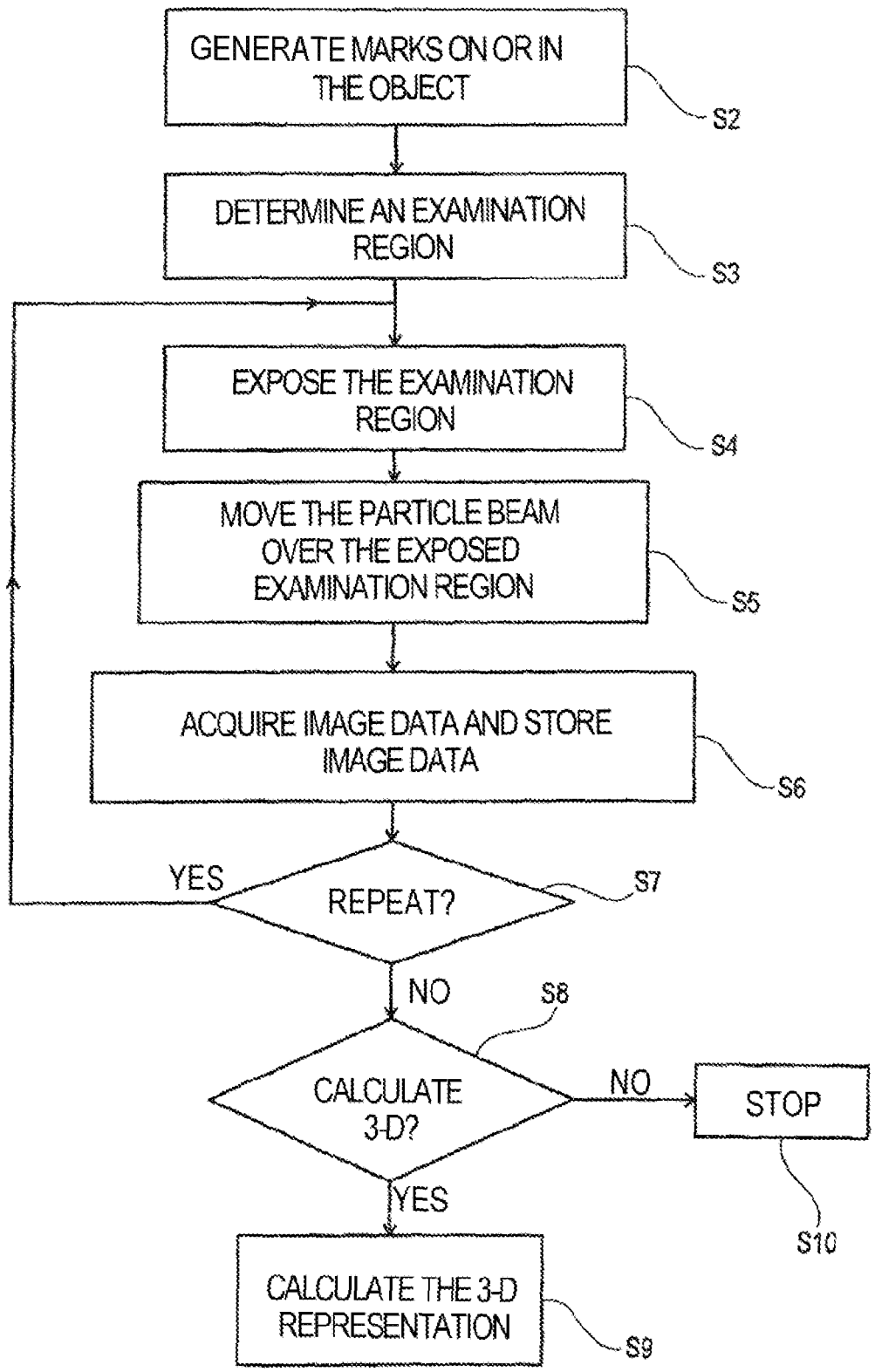
FIG. 4 shows a schematic illustration of a flow of a further embodiment of the method.

A sequence of a further exemplary embodiment of the method according to the system described herein is depicted in FIG. 4. The exemplary embodiment of FIG. 4 is based on FIG. 1A. In contrast to the exemplary embodiment in FIG. 1A, provision is made in the exemplary embodiment of FIG. 4 of the method step of introducing the object 100 into the support material 101 being dispensed with and of the marks 103 being generated directly in or on the object 100 in method step S2.

FIG. 5 shows a schematic illustration of an x-ray tomography system 400, which can be used for the embodiments of the method according to the system described herein. The x-ray tomography system 400 has a generation system 401 for x-ray radiation —i.e. an x-ray source —which generates x-ray beams 402. Furthermore, the x-ray tomography system 400 has a rotation table 403 with an object holder 418 for holding the object 100 and/or the support material 101. In some exemplary embodiments, the generator system 401 has integrated filters for filtering the x-ray beams 402.

If the object 100 and/or the support material 101 are irradiated by the x-ray beams 402, x-ray photons are transmitted through the object 100 and/or the support material 101. These transmitting x-ray photons form transmitting x-ray beams 404, which are detected by a detector system 405. In some exemplary embodiments, use is made of an objective lens to generate an image on the detector system 405.

A magnified projection image of the object 100 and/or of the support material 101 is generated at the detector system 405 with a magnification that is given by the ratio of a first distance 406 to a second distance 407. Here, the distance 406 corresponds to the distance between the generator system 401 and the object 100 and/or the support material 101. The second distance 407 corresponds to the distance between the object 100 and/or the support material 101 and the detector system 405. In order to obtain a particularly good high resolution of the x-ray tomography system 400, the detector system 405 has a highly resolving embodiment. Additionally, or as an alternative thereto, the object 100 and/or the support material 101 is/are arranged near the generator system 401, with the resolution of the x-ray image being limited by the resolution of the detector system 405, the size of the focused spot of the x-ray beam, the position of the object 100 and/or of the support material 101 and the geometric magnification.

In order to set the geometric magnification, a user can use interface applications 408 of a computer system 409 in order to set the first distance 406 and the second distance 407. The applicant sets the first distance 406 and the second distance 407 such that the desired magnification is obtained. The rotation table 403 is rotated in order to perform a computed tomography scan using a controller 410. The detector system 405 can be embodied in such a way that the image field at the object 100 and/or the support material 101 is adjustable by changing the pixel size in the detector system 405.

The detector system 405 generates an image of the x-ray photons in pixels of the transmitted x-ray beams 404, which interact with a scintillator in the detector system 405 and generate signals which are processed further. The image at the detector system 405 is also referred to as a projection, x-ray beam projection or x-ray beam projection image.

The computer system 409 comprises the already aforementioned interface applications 408 and the controller 410. Furthermore, the computer system 409 comprises an image processor 411. A display unit 412 is connected to the computer system 409 and displays information of the x-ray tomography system 400, for example by using the interface applications 408 of the computer system 409. An input unit 413, e.g. a computer mouse or a touchscreen, enables a dialog between the user, the computer system 409 and the display unit 412.

The computer system 409 loads information from, and stores information in, a data storage medium 414, which is connected to the computer system 409. The controller 410 has a first controller interface 415, which allows the user to control the x-ray tomography system 400, for example by way of a software control by means of the computer system 409.

The controller 410 controls components of the x-ray tomography system 400, which are provided with second controller interfaces 416. By way of example, these components comprise the image processor 411, the detector system 405, the rotation table 403 and the generator system 401 for x-ray radiation.

The user can define and/or select scanning parameters 417 for the computed tomography by using the interface applications 408. By way of example, the scan parameters 417 comprise the setting for the x-ray beam voltage, which is connected with the x-ray energy spectrum of the scan, and the exposition time of the generator system 401 for the x-ray radiation. By way of example, the user also selects settings in respect of the image field of the x-ray beams 402, which are incident on the object 100 and/or the support material 101, in respect of the number of x-ray projection images of the object 100 and/or of the support material 101 to be generated and in respect of the rotation angle, about which the rotation table 403 is intended to be rotated in the x-ray beam 402 in order to rotate the object 100 and/or the support material 101 in the case of an x-ray computed tomography scan.

Using the image processor 411, the computer system 409 processes the data records which are based on signals of the detector system 405, wherein one data record is in each case associated with a specific rotation angle. The image processor 411 generates a different projection image for each rotation angle of the rotation table 403 and, hence, of the object 100 and/or of the support material 101 and combines the generated projection images using a computed tomography reconstruction algorithm to form three-dimensional tomographic volume information about the object 100 and/or the support material 101.

As already mentioned above, the detector system 405 comprises e.g. a scintillator. In particular, provision is made of the detector system 405 being able to consist of e.g. scintillators sensitive to x-ray radiation with subsequent light detectors. The transmitting x-ray beam 404 then generates light in the scintillators, which is subsequently detected in a spatially resolved manner by the light detectors. In specific embodiments, an optical magnification system can be arranged between a scintillator and the spatially resolving light detector; in this embodiment there then is a light-optical magnification of the image generated on the scintillator by means of x-ray radiation.

In an alternative embodiment of the x-ray tomography system 400, an x-ray condenser, in particular a mirror condenser, can be arranged between the generator system 401 for x-ray beams—i.e. the x-ray source—and the object 100 and/or the support material 101, by means of which condenser the x-ray source 401 is imaged on or in the object 100 and/or the support material 101. An x-ray objective, in particular in the form of a Fresnel zone plate, can be arranged between, firstly, the object 100 and/or the support material 101 and, secondly, the detector system 405, by means of which x-ray objective the object 100 and/or the support material 101 is imaged in a magnified manner on the detector system 405, for example on a scintillator of the detector system 405. Such systems equipped with an x-ray condenser and an x-ray objective supply a higher spatial resolution than x-ray tomography systems based purely on projection.

The system described herein also relates to a further method for generating image data of an object by means of a particle beam, wherein the further method comprises the following steps:
- introducing the object into a transparent support material in such a way that the object is surrounded by the transparent support material;
- arranging at least one mark on the transparent support material;
- determining at least one examination region of the object;
- exposing the examination region by removing material of the object and/or of the transparent support material;
- guiding a first particle beam over the exposed examination region; and
- acquiring image data of the exposed examination region using at least one detector by detecting interaction particles and/or interaction radiation due to an interaction of the first particle beam with the exposed examination region.

In one embodiment of the further method, provision is additionally or alternatively made of the object being introduced into the transparent support material in such a way that the object is partly or completely surrounded by the transparent support material.

In a further embodiment of the further method, provision is additionally or alternatively made of the examination region of the object being determined relative to the marks.

In an in turn further embodiment of the further method, provision is additionally or alternatively made of the examination region of the object being determined with the aid of a tomographic method which supplies a three-dimensional data record of the object embedded in the transparent support material.

In an even further embodiment of the further method, provision is additionally or alternatively made of one of the following steps being carried out:
- the introduction of the object into the transparent support material comprises the introduction of the object into a glass and/or a transparent plastic;
- the introduction of the object into the transparent support material comprises the introduction of the object into a glass and/or a transparent plastic, which has a symmetric form; or
- the introduction of the object into the transparent support material comprises the introduction of the object into a glass and/or a transparent plastic, which has the shape of a cuboid and/or a cylinder.

In one embodiment of the further method, provision is additionally or alternatively made of at least one of the following steps being carried out:
- the mark is arranged at the transparent support material by means of a laser;
- the mark is arranged at the transparent support material by means of a second particle beam;
- the mark is arranged at the transparent support material on a surface of the transparent support material; or
- the mark is arranged by internal engraving of the transparent support material.

In a further embodiment of the further method, provision is additionally or alternatively made for at least one of the following steps being carried out:
- the examination region of the object is determined using an x-ray microscope; or
- the examination region of the object is determined using a confocal laser scanning microscope.

In an even further embodiment of the further method, provision is additionally or alternatively made of the examination region being exposed using a second particle beam.

In an in turn further embodiment of the further method, provision is additionally or alternatively made of the acquired image data of the exposed examination region being stored in a storage unit.

In one embodiment of the further method, provision is additionally or alternatively made of the acquired image data of the exposed examination region being acquired as first image data and wherein furthermore the following steps are carried out:
- storing the first image data in a storage unit;
- removing a layer of the object by means of a second particle beam;
- moving the first particle beam over the object after removing the layer of the object;
- acquiring second image data using the detector by detecting interaction particles and/or interaction radiation due to an interaction of the first particle beam with the object;
- storing the second image data in the storage unit; and
- calculating three-dimensional image data by means of the first image data and the second image data.

In a further embodiment of the further method, provision is additionally or alternatively made of an electron beam being used as the first particle beam.

In an in turn further embodiment of the further method, provision is additionally or alternatively made of an ion beam being used as the second particle beam.

The system described herein also relates to a further particle beam device for carrying out the further method, comprising
- at least one first beam generator for generating a first particle beam,
- at least one first objective lens for focusing the first particle beam onto the object, and
- at least one control unit comprising a processor, onto which a computer program product with executable program code is loaded and which upon execution executes at least one step of the further method.

All aforementioned methods and particle beam devices can be used e.g. for the examination of materials, in particular semiconductors. A region of interest is localized by means of x-ray radiation of an x-ray microscope. By way of example, a crack in the material or a defect in the semiconductor is localized. By way of example, the defect is an open electrical connection or a short circuit. The localized defect or the localized crack is the examination region, which is subsequently exposed and examined in more detail by means of the electron beam, as described above. Additionally, provision is made of a TEM lamella being generated by means of the ion beam, in which TEM lamella the examination region is arranged. By way of example, this TEM lamella can be removed from the material or the semiconductor (in particular by means of the so-called "lift out") and then examined further by means of a TEM examination.

All of the aforementioned methods and particle beam devices are e.g. used for examining objects in the oil industry and gas industry sectors. Examination regions are identified in an object by means of x-ray radiation of an x-ray microscope. By way of example, different phases in the object are determined in the process. Subsequently, there is a further analysis of the object for determining the rock-physical—that is to say petrophysical—properties of the object by way of examining the object by means of a scanning electron microscope and/or by means of an ion microscope and on the basis of the information obtained as a result of irradiating the object with x-ray radiation, which information can only supply a rough overview of the object because the resolution of the x-ray microscope is reduced compared to that of the scanning electron microscope.

All of the aforementioned methods and particle beam devices are e.g. used for examining biological objects. By way of example, a biological object, in particular a tissue sample, is initially examined using a confocal laser scanning microscope. Subsequently, the biological object can be prepared and/or stained in a manner suitable for electron microscopy. Subsequently, the biological object is affixed to an object holder. By way of example, the biological object is introduced into a support material, as already described further above. The biological object then is opaque to visible light. Examination regions, e.g. stained synaptic regions, are identified by means of x-ray radiation of an x-ray microscope. Subsequently there is an examination by means of the above-described methods and particle beam devices.

The features of the invention disclosed in the description above, in the drawings and in the claims can be essential, both individually and in any combination, for implementing the invention in the various embodiments thereof.

The invention claimed is:

1. A method for generating image data of an object using a particle beam, the method comprising:
    arranging at least one mark in the object or in a support material in which the object is embedded;
    determining a first examination region by transmitting beams through at least one of: the object and the support material;
    exposing the first examination region by removing material of at least one of: the object and the support material;
    guiding a first particle beam over the first examination region; and
    acquiring image data of the first examination region using at least one detector by detecting at least one of: interaction particles and interaction radiation due to an interaction of the first particle beam with the first examination region.

2. The method as claimed in claim 1, further comprising:
    introducing the object into the support material in such a way that the object is partly or completely surrounded by the support material.

3. The method as claimed in claim 2, wherein the support material is at least one of: glass and a transparent plastic.

4. The method as claimed in claim 3, wherein the support material has one of: a symmetric form, a cuboid form or a cylinder form.

5. The method as claimed in claim 1, wherein the first examination region of the object is determined relative to the mark.

6. The method as claimed in claim 1, wherein the first examination region is determined with a tomographic technique that supplies a three-dimensional data record of the object.

7. The method as claimed in claim 1, wherein the marks are arranged in such a way that at least some of the marks are present after the first examination region is exposed.

8. The method as claimed in claim 7, wherein the marks are attached in such a way that some of the marks present after exposing the first examination region are identifiable in the image data obtained by detecting interaction particles or interaction radiation due to an interaction of the first particle beam with the first examination region.

9. The method as claimed in claim 1, wherein the mark is provided by at least one of: a laser, a second particle beam, or internal engraving and wherein the mark is provided on or in the object or on or in the support material.

10. The method as claimed in claim 1, wherein the first examination region is determined using one of: an x-ray microscope or a confocal laser scanning microscope.

11. The method as claimed in claim 1, wherein the first examination region is exposed using a second particle beam.

12. The method as claimed in claim 11, wherein an ion beam is used as the second particle beam.

13. The method as claimed in claim 11, wherein a TEM lamella corresponding to the first examination region is generated using the second particle beam, the TEM lamella is irradiated by the first particle beam and wherein particles of the first particle beam transmitted through the TEM lamella are detected by a further detector.

14. The method as claimed in claim 1, wherein acquired image data of the first exposed examination region is stored in a storage unit.

15. The method as claimed in claim 1, wherein image data of the first examination region is acquired as first image data, the method further comprising:
    storing the first image data in a storage unit;
    removing a layer of the object using a second particle beam;
    moving the first particle beam over the object after removing the layer of the object;
    acquiring second image data using the detector to detect at least one of: interaction particles and/or interaction radiation due to an interaction of the first particle beam with the object;
    storing the second image data in the storage unit; and
    calculating three-dimensional image data using the first image data and the second image data.

16. The method as claimed in claim 1, wherein an electron beam is used as the first particle beam.

17. The method as claimed in claim 1, wherein the first examination region corresponds to a crack in a material or a defect of a semiconductor.

18. The method as claimed in claim 1, wherein determining the first examination region is effected using at least one of: light beams in the visible range and x-rays.

19. A method for generating image data of an object using a particle beam, comprising:
    arranging at least one mark in the object or in a support material in which the object is embedded;
    determining a first examination region using beams, wherein at least one of: the object and the support material are transparent to the beams;
    exposing the first examination region by removing material of at least one of: the object and the support material;
    guiding a first particle beam over the first examination region; and
    acquiring image data of the first examination region using at least one detector by detecting at least one of: interaction particles and interaction radiation due to an interaction of the first particle beam with the first examination region,
    wherein the first examination region is determined with a tomographic technique that supplies a three-dimensional data record of the object, and
    wherein the three-dimensional data record has a first spatial resolution R1, wherein the image data of the first examination region has a second spatial resolution R2, and wherein a ratio of the first spatial resolution to the second spatial resolution is greater than 5 and less than 10,000.

20. A method for generating image data of an object using a particle beam, comprising:
   arranging at least one mark in the object or in a support material in which the object is embedded;
   determining a first examination region using beams, wherein at least one of: the object and the support material are transparent to the beams;
   exposing the first examination region by removing material of at least one of: the object and the support material;
   guiding a first particle beam over the first examination region; and
   acquiring image data of the first examination region using at least one detector by detecting at least one of: interaction particles and interaction radiation due to an interaction of the first particle beam with the first examination region,
   wherein the first examination region is determined with a tomographic technique that supplies a three-dimensional data record of the object, and
   wherein the tomographic technique includes irradiating the object a number of times in succession using x-ray radiation at different angles of incidence of the x-ray radiation on the object and detecting a sequence of images with the x-ray radiation respectively transmitted through the object, establishing the three-dimensional data record of the object from a sequence of images by applying tomography evaluation software to the sequence of images, wherein the first examination region is determined in the three-dimensional data record of the object and wherein the marks are arranged in the object or in the support material in such a way that the marks are identifiable in the three-dimensional data record of the object.

21. A method for generating image data of an object using a particle beam, the method comprising:
   arranging at least one mark in the object or in a support material in which the object is embedded;
   determining a first examination region using beams, wherein at least one of: the object and the support material are transparent to the beams;
   exposing the first examination region by removing material of at least one of: the object and the support material;
   guiding a first particle beam over the first examination region; and
   acquiring image data of the first examination region using at least one detector by detecting at least one of: interaction particles and interaction radiation due to an interaction of the first particle beam with the first examination region,
   wherein the object is initially examined using a confocal laser scanning microscope and then stained and fixed and then the first examination region is determined using an x-ray microscope, the first examination region is exposed and image data of the first examination region is acquired.

22. A particle beam device, comprising:
   at least one first beam generator for generating a first particle beam;
   at least one first objective lens for focusing the first particle beam onto an object; and
   at least one control unit having a processor, onto which a computer program product with executable program code is loaded and which upon execution executes steps, including arranging at least one mark in the object or in a support material in which the object is embedded, determining a first examination region by transmitting beams through at least one of: the object and the support material, exposing the first examination region by removing material of at least one of: the object and the support material, guiding a first particle beam over the first examination region, and acquiring image data of the first examination region using at least one detector by detecting at least one of: interaction particles and interaction radiation due to an interaction of the first particle beam with the first examination region.

* * * * *

UNITED STATES PATENT AND TRADEMARK OFFICE
CERTIFICATE OF CORRECTION

PATENT NO. : 9,857,318 B2
APPLICATION NO. : 14/778343
DATED : January 2, 2018
INVENTOR(S) : Perez-Willard Page 1 of 1

It is certified that error appears in the above-identified patent and that said Letters Patent is hereby corrected as shown below:

In the Specification

Column 4, Lines 49-50, please replace "the object to the analyzed" with -- the object to be analyzed --

Column 10, Lines 53-54, please replace "transparent support material 1" with -- transparent support material 101 --

Column 10, Line 60, please replace "object 101" with -- object 100 --

Column 11, Line 7, please replace "object 101" with -- object 100 --

Column 11, Line 65, please replace "object 101" with -- object 100 --

Column 12, Lines 7-8, please replace "provision is additionally made" with -- provision is additionally or alternatively made --

Column 14, Line 22, please replace "method step 53A" with -- method step S3A --

Signed and Sealed this
Second Day of July, 2019

Andrei Iancu
*Director of the United States Patent and Trademark Office*